United States Patent [19]
Kieffer et al.

[11] Patent Number: 6,146,835
[45] Date of Patent: *Nov. 14, 2000

[54] HUMAN KAPPA OPIOID RECEPTOR, NUCLEIC ACIDS AND USES THEREOF

[75] Inventors: Brigitte Kieffer, Erstein-Krafft; Frederic Simonin, Bischheim, both of France

[73] Assignee: Universite Louis Pasteur, Strasbourg, France

[*] Notice: This patent issued on a continued prosecution application filed under 37 CFR 1.53(d), and is subject to the twenty year patent term provisions of 35 U.S.C. 154(a)(2).

[21] Appl. No.: 08/765,743

[22] PCT Filed: Jul. 7, 1995

[86] PCT No.: PCT/FR95/00912

§ 371 Date: Feb. 11, 1997

§ 102(e) Date: Feb. 11, 1997

[87] PCT Pub. No.: WO96/01898

PCT Pub. Date: Jan. 25, 1996

[30] Foreign Application Priority Data

Jul. 11, 1994 [FR] France .................................. 94 08531

[51] Int. Cl.⁷ ........................ C12N 15/12; C07K 14/705; G01N 33/53
[52] U.S. Cl. .......................... 435/7.1; 536/23.5; 530/350; 435/71.1; 435/71.2; 435/69.1; 435/32.1; 435/325; 435/252.3; 435/254.11; 435/471
[58] Field of Search .......................... 530/350; 435/69.1, 435/320.1, 325, 252.3, 254.11, 7.1, 71.1, 71.2, 471; 536/23.5, 24.31; 514/2

[56] References Cited

FOREIGN PATENT DOCUMENTS

WO 94/28132  12/1994  WIPO .

OTHER PUBLICATIONS

Miyuki Nishi et al., "cDNA Cloning and Pharmacological Characterization of an Opioid Receptor with High Affinities for κ–subtype–selective Ligands", pp. 77–80, vol. 330, No. 1, Sep. 1993, Federation of European Biochemical Societies.

Masabumi Minami et al., "Cloning and Expression of a cDNA for the Rat κ–Opioid Receptor", pp. 291–294, vol. 329, No. 3, Aug. 1993, Federation of European Biochemical Societies.

Kazuki Yasuda et al., "Cloning and Functional Comparison of κ and δ Opioid Receptors from Mouse Brain", pp. 6736–6740, vol. 90, Jul. 1993, Proc. Natl. Acad. Sci., USA, Neurobiology.

Erik Mannson, et al., "Isolation of a Human κ Opioid Receptor cDNA From Placenta", pp. 1431–1437, Biochemical and Biophysical Research Communications, vol. 202, No. 3, 1994.

Guo–xi Xie et al., "Primary Structure and Functional Expression of a Guinea Pig κ Opioid (dynorphin) Receptor", pp. 3779–3784, Proc. Natl. Acad. Sci. USA, vol. 91, Apr. 1994 Pharmacology.

Fan Meng et al., "Cloning and Pharmacological Characterization of a Rat κ Opioid Receptor", pp. 9954–9958, Proc. Natl. Acad. Sci. USA, vol. 90, Nov. 1993 Pharmacology.

Ahmed et al., Life Sciences, vol. 44, 861–871, 1989.

*Primary Examiner*—Prema Mertz
*Attorney, Agent, or Firm*—Young & Thompson

[57] ABSTRACT

Novel peptides having human kappa opioid receptor activity, genetic material for expressing same, any recombinant cell expressing said polypeptides, and use thereof.

5 Claims, 2 Drawing Sheets

Reaction 1: Amplification of the portion 3' of ADNc ---> fragment 1 (760 bp)

Reaction 2: Amplification of the portion 5' of ADNc ---> fragment 2 (508 bp)

Reaction 3: Assembly of the two portions of ADNc by means of an EcoR I site in position 365.

HUMAN KAPPA OPIOID RECEPTOR, NUCLEIC ACIDS AND USES THEREOF

The present invention relates to new polypeptides and the genetic material permitting their expression. More particularly, it relates to new polypeptides having a human kappa opioid receptor activity.

Opioid receptors are membranous receptors of the nervous system which modulate the analgesic and psychotropic properties of alkaloid drugs of the morphine type (Brownstein, 1993, Proc. Natl. Acad. Sci. USA, Vol. 90, 5391). Pharmacological studies have demonstrated the existence of three subtypes of receptors, called mu, delta and kappa, which differ by their capacity to bind to different opioid ligands (Goldstein et al., 1989, Mol. Pharmacol., Vol. 36, 265–272) and by their distribution in the organism (Mansour et al., 1987, J. Neurosci., Vol. 7, 2445). Recently, three opioid receptors have been cloned in rodents. The pharmacological profile of these three cloned receptors, expressed transitorily in Cos cells, indicate that there is a delta receptor, a mu receptor and a kappa receptor. Analysis of their primary structure confirms that they are part of the family of receptors coupled to the G proteins, which have a putative topology with seven transmembranal domains (Bockaert, 1991, Curr. Op. Neurobiol., Vol. 1, 32).

The present invention comprises the elucidation, isolation and molecular characterization of the human kappa opioid receptor. It comprises particularly the isolation and sequencing of the gene coding for this receptor, in the construction of recombinant strains permitting the expression of functional receptors, and in the elaboration of tests permitting the isolation of compounds active on these receptors and having desirable therapeutic properties. The DNA sequences of the invention also permit the provision of probes capable of detecting in biological specimens any irregularity in the expression of a kappa opioid receptor (non-expression, mutation, polymorphism, etc.). These probes are also usable for cloning by hybridization of any other cDNA coding for an opioid receptor, from tissues of diverse origins and particularly of human origin.

A first object of the invention therefore resides in a nucleotide sequence coding for a polypeptide having a human kappa opioid receptor activity.

More preferably, the nucleotide sequence according to the invention is selected from:

(a) all or a portion of the nucleotide SEQ ID No. 1 or of its complementary strand, (b) any sequence hybridizing with a sequence (a) and coding for a polypeptide having human kappa opioid receptor activity, and, (c) sequences derived from sequences (a) and (b) by degeneration of the genetic code.

The different nucleotide sequences of the invention can be of artificial origin or not. They can be genome sequences, cDNA sequences, RNA sequences, hybrid sequences or synthetic or semi-synthetic sequences. These sequences can be obtained for example by screening DNA banks (cDNA bank, DNA genome bank) by means of probes developed on the basis of the sequence SEQ ID No. 1. Such banks can be prepared from cells of different origins by conventional bimolecular techniques known to those in the art. The nucleotide sequences of the invention can also be prepared by chemical synthesis, particularly according to the phosphoramidites method, or again by mixed methods including chemical or enzymatic modification of sequences obtained by scanning banks.

The nucleotide sequences of the invention can be used for the production of kappa opioid polypeptides. The term kappa opioid polypeptide designates any polypeptide having a kappa opioid receptor activity, and any fragment or derivative of such a polypeptide. For the production of kappa opioid polypeptides, the coding portion for said polypeptide is generally placed below the signal control permitting its expression in a cellular host. The choice of these signals (promoters, terminators, etc.) can vary as a function of the cellular host utilized. To this end, the nucleotide sequences of the invention can be a part of a vector, which can have autonomous or integrated replication. More particularly, the autonomous replication vectors can be prepared by using autonomous replication sequences in the selected host. Acting on the integrative vectors, these latter can be prepared for example by using sequences homologous to certain regions of the genome of the host, permitting by homologous recombination, the integration of the vector. The cellular hosts usable for the production of the opioid polypeptides of the invention by recombinant means, can be either the eucaryote hosts or procaryote hosts. Among the eucaryote hosts which are suitable, can be cited animal cells, yeasts, or mushrooms. In particular, for yeasts, can be cited the yeasts of the type Saccharomyces, Kluyveromyces, Pichia, Schwanniomyces, or Hansenula. As to the animal cells, can be cited the cells COS, CHO, C127, NIH-3T3, etc. As to mushrooms, can be cited more particularly Aspergillus ssp. or Trichoderma ssp. As procaryote hosts, it is preferred to use the following bacteria: *E.coli*, Bacillus, or Streptomyces.

The nucleotide sequences of the present invention are also usable in the pharmaceutical field, either for the production of anti-directional sequences usable in the field of gene therapy, or for the production of probes permitting the detection, by hybridation experiments, of the expression of opioid receptors in biological specimens and the elaboration of genetic anomalies (polymorphism, mutations) or of aberrant expressions.

The inhibition of the expression of certain genes by anti-directional sequences is thought to be a promising strategy in the control of the activity of a gene. The anti-directional sequences are sequences whose transcription product is complementary to the strand coding a given gene, and is thus capable of specifically hybridizing with the transcribed mRNA, inhibiting its translation into protein (EP140 308). The invention thus has for its object anti-directional sequences capable of inhibiting at least partially the production of kappa opioid polypeptides such as defined above. Such sequences can be constituted by all or a portion of the nucleotide sequences defined above. It relates generally to sequences or to fragments of sequences complementary to the sequences coding for peptides of the invention. Such sequences can be obtained from the sequence SEQ ID No. 1, by fragmentation, etc. or by chemical synthesis.

As indicated above, the invention also permits the provision of nucleotide probes, synthetic or not, capable of hybridizing with the nucleotide sequences defined above which code for the opioid polypeptides of the invention, or with the corresponding mRNA. Such probes can be used in vitro as diagnostic tools, for the detection of the expression of a kappa opioid receptor, or for the elaboration of genetic anomalies (poor splicing, polymorphism, point mutations, etc.). Given the multiple activities of the endogenous ligands of the opioid receptors, the probes of the invention can thus permit identifying neurological, cardiovascular or psychiatric afflictions. These probes can also be used for the elaboration and isolation of homologous nucleic acid sequences coding for opioid polypeptides as defined above, from other cells sources and preferably from cells of human origin. The probes of the invention generally comprise at least 10 bases, and they can comprise up to all of the sequence SEQ ID No. 1 or its complementary strand. Preferably, the probes are, before their use, marked. To do that, different techniques known to those in the art can be used (radioactive marking, enzymatic marking, etc.). The conditions of hybridation under which these probes can be used are indicated in the general cloning technique hereinafter as well as in the examples.

The invention also has for its object any polypeptide resulting from the expression of a nucleotide sequence as defined above. Preferably, it is a polypeptide comprising all or a portion of the polypeptide sequence SEQ ID No. 1 or of a derivative of the latter.

In the meaning of the present invention, the term derived designates any molecule obtained by modification of the genetic and/or chemical nature of the polypeptide sequence SEQ ID No. 1 and retaining a kappa opioid receptor activity. By modification of genetic and/or chemical activity is meant any mutation, substitution, deletion, addition and/or modification of one or several residues. Such derivatives can be generated for different purposes, such as particularly to augment the affinity of the peptide for its ligand or ligands, to improve its production level, to increase its resistance to proteases, to increase and/or modify its activity, or to give it new pharmacokinetic and/or biological properties. Among the derivatives resulting from an addition, can be cited for example the chimeral polypeptides comprising a supplemental heterological portion connected at one end.

Preferably, the polypeptides of the invention are polypeptides having the capacity to bind dynorphine and the derivatives of the type of prodynorphine. More preferably, they have the capability of binding agonists of dynorphine such as U-50,488, ethylcetocyclasoncine and bremozacine, and the antagonists of the dynorphine such as norbinaltorphimine. According to a preferred embodiment, the polypeptides of the invention are adapted to be recognized by antibodies recognizing the complete peptide sequence of SEQ ID No: 2. Such antibodies can be generated by any technique known to those in the art, by using as antigens the polypeptides described in the present application.

As indicated in the examples, these polypeptides can be expressed in different cell types to form functional opioid receptors.

The polypeptides of the invention can be obtained by expression in a cellular host of a nucleotide sequence such as described above, by chemical synthesis, on the basis of the SEQ ID No. 1 sequence, by using techniques known to those in the art, or by a combination of these techniques.

Another object of the invention concerns recombinant cells capable of expressing at their surface a polypeptide having a human kappa opioid receptor activity. These cells can be obtained by introduction of a nucleotide sequence as defined above, then by culturing said cells under conditions for the expression of said sequence.

The recombinant cells according to the invention can also be eucaryote or procaryote cells. Among the eucaryote cells which are suitable, can be cited animal cells, yeasts, or mushrooms. In particular, for yeasts can be cited the yeasts of the type Saccharomyces, Kluyveromyces, Pichia, Schwanniomyces, or Hansenula. As to animal cells, can be cited the cells COS, CHO, C127, NIH-3T3, etc. For mushrooms can be cited more particularly Aspergillus ssp. or Trichoderma ssp. As procaryote hosts, it is preferred to use the following bacteria: *E.coli*, Bacillus, or Streptomyces. The cells thus obtained can be used for measuring the capacity of different molecules to be used as ligands or as modulators of the activity of the opioid receptors. More particularly, they can thus be used in a procedure for elaborating and isolating ligands or for modulating the activity of opioid receptors, and more preferably, agonists and antagonists.

Another object of the invention hence relates to the process of elaborating and/or isolating ligands of the opioid receptors, according to which the following steps are performed:

there is placed in contact a molecule or a mixture containing different molecules, if desired unidentified, with a recombinant cell such as described above expressing at its surface a polypeptide having an opioid receptor activity under conditions permitting interaction between said polypeptide and said molecule in the case in which the latter has an affinity for said polypeptide, and detecting and/or isolating the molecules bound to said polypeptide.

In a particular embodiment, this process of the invention is adapted for the elaboration and/or isolation of agonists and antagonists of dynorphine or other ligands of the kappa receptors for the kappa opioid receptors.

Another object of the invention relates to a process for elaborating and/or isolating modulators of the opioid receptors, according to which the following steps are performed:

a molecule or a mixture containing different molecules, if desired unidentified, is placed in contact with a recombinant cell such as described above expressing at its surface a polypeptide having an opioid receptor activity, in the presence of the endogenous ligand of said receptor, under conditions permitting interaction between said polypeptide and its ligand, and there are detected and/or isolated the molecules capable of modulating the activity of the ligand on said polypeptide.

In a particular embodiment, this process of the invention is adapted for the elaboration and/or isolation of modulators of the activity of dynorphine or other ligands of the kappa receptors on the kappa opioid receptors.

Another object of the invention is the use of a ligand or a modulator identified and/or obtained according to the process described above, as a medication. Such ligands or modulators can thus permit treating certain afflictions connected to the opioid receptors. In particular, the kappa opioid receptors being mediators of an analgesic effect, the agonists of these receptors can be used to decrease the sensations of pain.

The invention also relates to any medication comprising as active principle at least one molecule acting on a receptor of the invention. Preferably, the molecule is a ligand or a modulator identified and/or isolated according to the process described above.

Other advantages of the present invention will become apparent from a reading of the examples which follow, which are to be considered as illustrative and not limiting.

GENERAL TECHNIQUES FOR CLONING

Conventional methods used in molecular biology such as preparative extractions of plasmid DNA, the centrifugation of plasmid DNA in a gradient of cesium chloride, electrophoresis on agarose or acrylamide gels, purification of DNA fragments by electroelution, extractions of proteins with phenol or phenol-chloroform, the precipitation of DNA in saline medium by ethanol or isopropanol, transformation with *Escherichia coli*, etc., are well known to those skilled in the art and are plentifully described in the literature [Maniatis T. et al., "Molecular Cloning, a Laboratory Manual", Cold Spring Harbor Laboratory, Cold Spring Harbor, N.Y. 1982; Ausubel F. M. et al. (eds), "Current Protocols in Molecular Biology", John Wiley & Sons, New York, 1987].

For binding, the DNA fragments are separated according to their size by electrophoresis on agarose or acrylamide gels, extracted with phenol or by a phenol/chloroform mixture, precipitated in ethanol, then incubated in the presence of DNA ligase of phage T4 according to the directions of the supplier.

Filling the protruding ends 5' is effected by the Klenow fragment of DNA of Polymerase. I *E.coli* according to the directions of the supplier. The destruction of the projecting ends 3' is effected in the presence of DNA Polymerase of T4 phage utilized according to the instructions of the supplier. The destruction of the projecting 5' ends is carried out by a treatment provided by S1 nuclease.

Mutagenesis directed in vitro by synthetic oligodeoxynucleotides is carried out according to the method developed by Taylor et al. [Nucleic Acids Res. 13 (1985) 8749–8764].

Enzymatic amplification of the DNA fragments is carried by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350].

Verification of the nucleotide sequences is carried out by the method developed by Sanger et al. [Proc. Natl. Acad. Sci. USA, 74 (1977) 5463–5467].

For hybridation experiments, the control conditions are based on Maniatis T. et al., above.

1. Genomic Cloning and Partial Organization of the Gene

A human genome bank has been scanned with the help of a cDNA probe coding for the delta receptor of mice (Kieffer et al., PNAS 1992, Vol. 89, 12048). The probe is a cDNA fragment Pst I-Not I (976 bp) which corresponds to most of the coding portion of cDNA. The bank was spread out and transferred onto nitrocellulose filters. These latter were hybridized with a probe marked with $^{32}P$, under relatively stringent conditions (5×SSC, 5×Denhardt's, SDS 0.1%, Formamide 40%, NaPPi 0.05% and DNA of salmon sperm 100 μg/ml). Washing was carried out with 0.1% SSC at 50° C. and the filters exposed to an X-ray film overnight.

Figure 1:
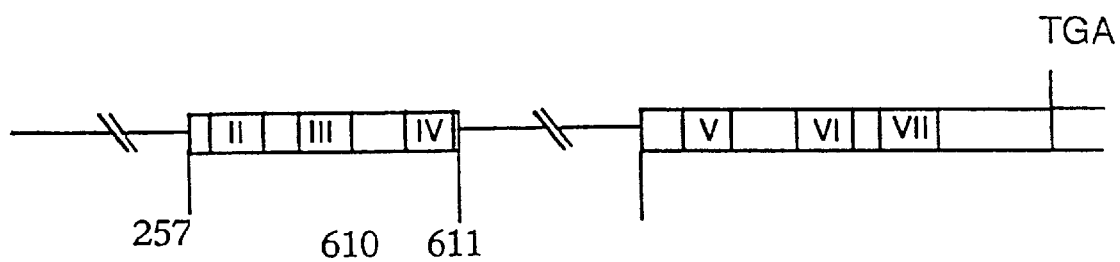
FIG. 1: Partial organization of the gene of the human kappa opioid receptor (hKOR). The exons are indicated by boxes and the introns by lines. The position of the putative transmembranal domains of the kappa receptor are indicated by Roman numerals. The known ends of the exons are numerically designated by Arabic numerals, relative to their position in cDNA (FIG. 2). The exon in 3' has been sequenced to the terminal codon TGA.

Two genomic clones hybridizing weakly with the probe were isolated. The analysis of the inserts by partial sequencing indicates that they contain regions very homologous to the kappa receptor of mice. An exon was identified in each clone: one codes for the corresponding topological region at the beginning of the first intracellular loop to the end of the second transmembranal domain, and the other codes for the rest of the C-terminal end of the receptor. The topology of this portion of the gene is shown in FIG. 1 and the exact position of the intron-exon junctions is indicated thereon.

2. Cloning of a Complete cDNA Coding for the Human Kappa Receptor

Most of the methods used ("standard"), except recited in the text, derive from Sambrook, J. et al., 1989 Molecular Cloning: A Laboratory Manual (Cold Spring Harbor Lab., Cold Spring Harbor, N.Y.), 2nd Ed.

The human placenta expresses the kappa receptor (Meunier et al., 1988 Life Sci., Vol. 43, 559). We have prepared the total RNA of the human placenta (Chomczynski, P. et al., 1987, Anal. Biochem., Vol. 162, 156) and have synthesized cDNA from this RNA, with the help of a random nucleotide trigger ("random hexamer", Pharmacia) and with the aid of Moloney Murine Leukemia Virus reverse transcriptase (BRL), under standard conditions.

We have then amplified the cDNA coding for the human kappa receptor by PCR (Polymerase Chain Reaction) by using portions of the human sequence obtained from the analysis of the genomic clones for the conception of specific triggers. THE 5' end of the coding portion of the gene being lacking, we have used an oligonucleotide derived from a kappa sequence of mice, for amplification from the end 5' end.

Figure 2:
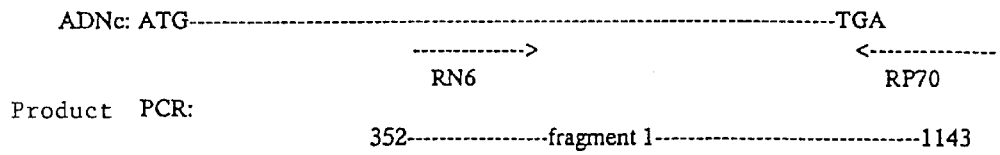
FIG. 2: Strategy for cloning cDNA coding for the human kappa opioid receptor.
Figure 2:
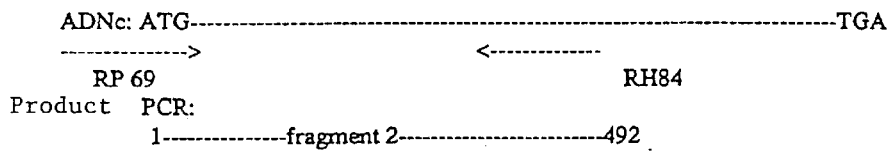
Figure 2:
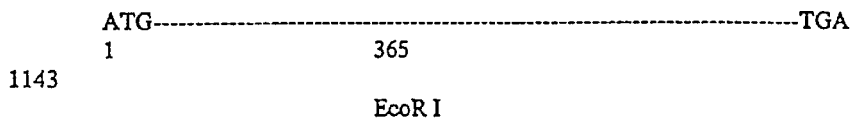

The use of two triggers located at the 5' (mice) and 3' (human) termini of the coding region being apparently less effective for the production of a complete cDNA, we have proceeded in three steps and the strategy used is shown in FIG. 2 (the figures indicate the precise position of the nucleotides in the complete sequence of cDNA shown in the sequence SEQ ID No. 1).

The sequence of the oligonucleotides utilized is as follows:

RP69: 5' GAGAGCTCGCGGCCGCGAGCTG-CAGCGCTCACCATG (SEQ ID No. 2)

RH84: 5' CACGGGGTGGCACACGGCAA (SEQ ID No. 4)

RN6: 5' GTCTACTFGATGAATWCCTGG (SEQ ED No. 5)

RP70: 5' AGACCCAAGCTTGCCCGGGTCCACGAC-TAGTCATACTGG (SEQ ID No. 6)

The sequences hybridizing to cDNA are indicated in fat, the other nucleotides being present to facilitate the ultimate step of cloning the fragments produced by the reaction of PCR.

The oligonucleotides RP70, RH84 and RN6 are derived from the human kappa sequence. The oligonucleotide RP69 corresponds to a sequence 5' not coding for mice (including the ATG initiator at the 3' end) so as not to introduce a murine sequence in human cDNA. The precise position of the regions of cDNA which hybridize to the four triggers is indicated in FIG. 2

The different amplification reactions have been carried out under the following conditions:

Reaction 1: Triggers RN6 and RP70. The reaction is carried out in the presence of Taq Polymerase (Cetus) under standard PCR conditions, except for the addition of 5% DMSO into the incubation medium. The amplification takes place for 40 cycles (1 minute at 94° C., 1 minute at 55° C., 1 minute at 72° C.). The last stage of elongation is carried out for 10 minutes at 720C. There is thus obtained A DNA fragment of the desired size (760 bp)=fragment 1.

Reaction 2: The amplification conditions are the same as for reaction 1. Two successive amplifications were necessary: the first uses the triggers RP69 and RP70 and leads to the obtention of a mixture of fragments of DNA of a size comprised between 1 and 1.3 kb, containing complete cDNA. This mixture is purified after electrophoresis on a 1% agarose gel by the GeneClean process and reamplified with the aid of oligonucleotides RP69 and RH84. There is thus obtained a fragment of DNA of a desired size (508 bp)= fragment 2.

Cloning of Complete cDNA:

The PCR fragments are stitched and cloned in the free ends of the pBluescript vector (Strategene) linearized with EcoR V. The inserts are sequenced in the two directions on an automatic DNA sequencer (373A DNA, Applied Biosystems Inc.). Then the two inserts are excised from the plasmid in the presence of EcoR I (cut side 3' of fragment 2 and side 5' of fragment 1) and of a restriction enzyme of the polylinker. The fragments are purified with 1% agarose gel by the GeneClean process and coligated in the vector pcDNA/Amp (Invitrogen) for the transitory expression of the receptor of Cos cells.

The two amplification reactions have produced the desired fragments 1 and 2. In the case of fragment 2, the use of an oligonucleotide derived from a mouse series at end 5' has permitted the amplification of human cDNA.

The two fragments cover themselves on 140 bp. The covering sequence is identical for the two fragments. The sequences of the two fragments are compared to the predetermined sequence from genomic DNA (position 257 to position 1143) and found to be perfectly identical. Concerning the portion of sequence 1 to 256, whose genome sequence is unknown to us, we have verified that the amplification with PCR has not introduced errors: we have compared the sequence of fragment 2 obtained from the three different amplification reactions and have found them identical in the three cases.

The cDNA sequence coding for the human kappa receptor according to the invention, as well as the derived protein sequence (SEQ ID NO: 2), are present in the sequence SEQ ID No. 1.

3. Conclusion: Primary Structure of the Human Kappa Receptor

We have used a probe coding for a delta opioid rector in mice so as to scan a human genome bank carefully and to isolate the homologous DNA genome fragments.

We have identified two exons which by comparison of sequence, code apparently for the human kappa opioid receptor. We have isolated an cDNA drive from this gene (coding portion) from a human tissue (placenta) and we have analyzed its primary structure (SEQ ID No. 1).

cDNA has a size of 1101 base pairs and codes for a protein with 380 amino acids. The nucleotide sequence is homologous to 86.7% to mouse cDNA coding for a kappa opioid receptor. The greatest regions of divergence are situated in the regions of the N- and C-terminals. These same regions are also the least conserved regions between the three subtypes mu, delta and kappa.

4. Pharmacological Study of the Receptor K56

The vector pcDNA/Amp containing the cDNA coding for the opioid receptor according to the invention isolated in Example 2 is used to transfect Cos-1 cells. The membranes of the transfected cells obtained are then prepared and tested for their capacity to bind certain marked opioid ligands.

The plasmid vector pcDNA/Amp purified with cesium chloride is used to transfect the Cos-1 cells by using the technique of DEAE-dextran.

72 hours after transfection, the recombinant cells are gathered and the membranes are prepared in the following manner: the cellular bottoms are gathered, at 4° C., in 60 ml of a buffer Tris-HCl 50 mM pH 7.4; EDTA 10 mM, homogenized and centrifuged at 1100 g for 10 minutes. The base is then taken up a second time in 30 ml of the same buffer, homogenized and centrifuged. The 2 supernatants are combined and centrifuged at 110,000 g for 15 minutes. The membranous base is then taken up in 5 ml of the same buffer, aliquoted and stored at −80° C. The experiments for a combination at saturation and for competition are then carried out on these membranes in the presence of different ligands. For that, the specimens of membrane (15–30 µg of proteins) are incubated 2 hours at 25° C. in the presence of $^3$H-diprenorphine or $^3$H-U-69,593, with or without a competitor, in a final volume of 1 ml of buffer Tris-HCl 50 mM (pH 7.4); EDTA 10 mM. The reaction is then stopped by filtration under vacuum on Whatman GF/B filters, and rinsed 3 times with 3 ml of cold buffer. The values of Ki are obtained by following the equation of Cheng and Prusso Ki=IC50/(1+L/Kd). The radioactivity has been measured with a β counter.

What is claimed is:

1. An isolated and purified nucleic acid comprising a nucleotide sequence selected from the group consisting of:

SEQ ID NO:1, and its complementary strand.

2. The nucleic acid according to claim 1, further comprising a sequence encoding a signal peptide.

3. A host cell transfected or transformed with the nucleic acid of claim 1 comprising SEQ ID NO:2.

4. A method for detecting ligands that bind to kappa opioid receptors, comprising the following steps:

contacting a test opioid ligand with a host cell according to claim 3, wherein said cell expresses a human kappa opioid receptor at its surface, under conditions which permit interaction between said polypeptide and said test opioid ligand, and detecting an opioid ligand bound to said polypeptide.

5. An isolated kappa opioid receptor free from other naturally-occurring proteins and comprising SEQ ID NO:2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1142 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1142

(xi) SEQUENCE DESCRIPTION: SEQ ID NO:1:

ATG GAC TCC CCG ATC CAG ATC TTC CGC GGG GAG CCG GGC CCT ACC TGC    48

```
Met Asp Ser Pro Ile Gln Ile Phe Arg Gly Glu Pro Gly Pro Thr Cys
 1               5                  10                 15

GCC CCG AGC GCC TGC CTG CCC CCC AAC AGC AGC GCC TGG TTT CCC GGC    96
Ala Pro Ser Ala Cys Leu Pro Pro Asn Ser Ser Ala Trp Phe Pro Gly
         20                  25                  30

TGG GCC GAG CCC GAC AGC AAC GGC AGC GCC GGC TCG GAG GAC GCG CAG   144
Trp Ala Glu Pro Asp Ser Asn Gly Ser Ala Gly Ser Glu Asp Ala Gln
             35                  40                  45

CTG GAG CCC GCG CAC ATC TCC CCG GCC ATC CCG GTC ATC ATC ACG GCG   192
Leu Glu Pro Ala His Ile Ser Pro Ala Ile Pro Val Ile Ile Thr Ala
 50                  55                  60

GTC TAC TCC GTA GTG TTC GTC GTG GGC TTG GTG GGC AAC TCG CTG GTC   240
Val Tyr Ser Val Val Phe Val Val Gly Leu Val Gly Asn Ser Leu Val
 65                  70                  75                  80

ATG TTC GTG ATC ATC CGA TAC ACA AAG ATG AAG ACA GCA ACC AAC ATT   288
Met Phe Val Ile Ile Arg Tyr Thr Lys Met Lys Thr Ala Thr Asn Ile
                 85                  90                  95

TAC ATA TTT AAC CTG GCT TTG GCA GAT GCT TTA GTT ACT ACA ACC ATG   336
Tyr Ile Phe Asn Leu Ala Leu Ala Asp Ala Leu Val Thr Thr Thr Met
             100                 105                 110

CCC TTT CAG AGT ACG GTC TAC TTG ATG AAT TCC TGG CCT TTT GGG GAT   384
Pro Phe Gln Ser Thr Val Tyr Leu Met Asn Ser Trp Pro Phe Gly Asp
         115                 120                 125

GTG CTG TGC AAG ATA GTA ATT TCC ATT GAT TAC TAC AAC ATG TTC ACC   432
Val Leu Cys Lys Ile Val Ile Ser Ile Asp Tyr Tyr Asn Met Phe Thr
 130                 135                 140

AGC ATC TTC ACC TTG ACC ATG ATG AGC GTG GAC CGC TAC ATT GCC GTG   480
Ser Ile Phe Thr Leu Thr Met Met Ser Val Asp Arg Tyr Ile Ala Val
145                 150                 155                 160

TGC CAC CCC GTG AAG GCT TTG GAC TTC CGC ACA CCC TTG AAG GCA AAG   528
Cys His Pro Val Lys Ala Leu Asp Phe Arg Thr Pro Leu Lys Ala Lys
                 165                 170                 175

ATC ATC AAT ATC TGC ATC TGG CTG CTG TCG TCA TCT GTT GGC ATC TCT   576
Ile Ile Asn Ile Cys Ile Trp Leu Leu Ser Ser Ser Val Gly Ile Ser
             180                 185                 190

GCA ATA GTC CTT GGA GGC ACC AAA GTC AGG GAA GAC GTC GAT GTC ATT   624
Ala Ile Val Leu Gly Gly Thr Lys Val Arg Glu Asp Val Asp Val Ile
         195                 200                 205

GAG TGC TCC TTG CAG TTC CCA GAT GAT GAC TAC TCC TGG TGG GAC CTC   672
Glu Cys Ser Leu Gln Phe Pro Asp Asp Asp Tyr Ser Trp Trp Asp Leu
 210                 215                 220

TTC ATG AAG ATC TGC GTC TTC ATC TTT GCC TTC GTG ATC CCT GTC CTC   720
Phe Met Lys Ile Cys Val Phe Ile Phe Ala Phe Val Ile Pro Val Leu
225                 230                 235                 240

ATC ATC ATC GTC TGC TAC ACC CTG ATG ATC CTG CGT CTC AAG AGC GTC   768
Ile Ile Ile Val Cys Tyr Thr Leu Met Ile Leu Arg Leu Lys Ser Val
                 245                 250                 255

CGG CTC CTT TCT GGC TCC CGA GAG AAA GAT CGC AAC CTG CGT AGG ATC   816
Arg Leu Leu Ser Gly Ser Arg Glu Lys Asp Arg Asn Leu Arg Arg Ile
             260                 265                 270

ACC AGA CTG GTC CTG GTG GTG GTG GCA GTC TTC GTC GTC TGC TGG ACT   864
Thr Arg Leu Val Leu Val Val Val Ala Val Phe Val Val Cys Trp Thr
         275                 280                 285

CCC ATT CAC ATA TTC ATC CTG GTG GAG GCT CTG GGG AGC ACC TCC CAC   912
Pro Ile His Ile Phe Ile Leu Val Glu Ala Leu Gly Ser Thr Ser His
 290                 295                 300

AGC ACA GCT GCT CTC TCC AGC TAT TAC TTC TGC ATC GCC TTA GGC TAT   960
Ser Thr Ala Ala Leu Ser Ser Tyr Tyr Phe Cys Ile Ala Leu Gly Tyr
305                 310                 315                 320
```

```
ACC AAC AGT AGC CTG AAT CCC ATT CTC TAC GCC TTT CTT GAT GAA AAC      1008
Thr Asn Ser Ser Leu Asn Pro Ile Leu Tyr Ala Phe Leu Asp Glu Asn
                325                 330                 335

TTC AAG CGG TGT TTC CGG GAC TTC TGC TTT CCA CTG AAG ATG AGG ATG      1056
Phe Lys Arg Cys Phe Arg Asp Phe Cys Phe Pro Leu Lys Met Arg Met
            340                 345                 350

GAG CGG CAG AGC ACT AGC AGA GTC CGA AAT ACA GTT CAG GAT CCT GCT      1104
Glu Arg Gln Ser Thr Ser Arg Val Arg Asn Thr Val Gln Asp Pro Ala
        355                 360                 365

TAC CTG AGG GAC ATC GAT GGG ATG AAT AAA CCA GTA     TG               1142
Tyr Leu Arg Asp Ile Asp Gly Met Asn Lys Pro Val
    370                 375                 380
```

(2) INFORMATION FOR SEQ ID NO:2:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Ser Pro Ile Gln Ile Phe Arg Gly Glu Pro Gly Pro Thr Cys
  1               5                  10                  15

Ala Pro Ser Ala Cys Leu Pro Pro Asn Ser Ser Ala Trp Phe Pro Gly
                 20                  25                  30

Trp Ala Glu Pro Asp Ser Asn Gly Ser Ala Gly Ser Glu Asp Ala Gln
             35                  40                  45

Leu Glu Pro Ala His Ile Ser Pro Ala Ile Pro Val Ile Ile Thr Ala
         50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
                100                 105                 110

Pro Phe Gln Ser Thr Val Tyr Leu Met Asn Ser Trp Pro Phe Gly Asp
            115                 120                 125

Val Leu Cys Lys Ile Val Ile Ser Ile Asp Tyr Tyr Asn Met Phe Thr
130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ser Ser Ser Val Gly Ile Ser
                180                 185                 190

Ala Ile Val Leu Gly Gly Thr Lys Val Arg Glu Asp Val Asp Val Ile
            195                 200                 205

Glu Cys Ser Leu Gln Phe Pro Asp Asp Asp Tyr Ser Trp Trp Asp Leu
        210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270
```

```
Thr Arg Leu Val Leu Val Val Ala Val Phe Val Val Cys Trp Thr
        275                 280                 285

Pro Ile His Ile Phe Ile Leu Val Glu Ala Leu Gly Ser Thr Ser His
        290                 295                 300

Ser Thr Ala Ala Leu Ser Ser Tyr Tyr Phe Cys Ile Ala Leu Gly Tyr
305                 310                 315                 320

Thr Asn Ser Ser Leu Asn Pro Ile Leu Tyr Ala Phe Leu Asp Glu Asn
                325                 330                 335

Phe Lys Arg Cys Phe Arg Asp Phe Cys Phe Pro Leu Lys Met Arg Met
                340                 345                 350

Glu Arg Gln Ser Thr Ser Arg Val Arg Asn Thr Val Gln Asp Pro Ala
                355                 360                 365

Tyr Leu Arg Asp Ile Asp Gly Met Asn Lys Pro Val
                370                 375                 380

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

GAGAGCTCGC GGCCGCGAGC TGCAGCGCTC ACCATG                                   36

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

CACGGGGTGG CACACGGCAA                                                     20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GTCTACTTGA TGAATTCCTG G                                                   21

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: cDNA
```

-continued (xi) SEQUENCE DESCRIPTION: SEQ ID NO:6:

AGACCCAAGC TTGCCCGGGT CCACGACTAG TCATACTGG           39